(12) United States Patent  (10) Patent No.: US 6,484,557 B1
Kang  (45) Date of Patent: Nov. 26, 2002

(54) SLIDE-TYPED SWITCH DURABILITY TESTING APPARATUS FOR AUTOMOBILE

(75) Inventor: Hee Won Kang, Ulsan (KR)

(73) Assignee: Hyundai Motor Company, Seoul (KR)

( * ) Notice: Subject to any disclaimer, the term of this patent is extended or adjusted under 35 U.S.C. 154(b) by 0 days.

(21) Appl. No.: 09/470,933

(22) Filed: Dec. 22, 1999

(30) Foreign Application Priority Data

Dec. 24, 1998 (KR) .......................... 98-058378
Dec. 24, 1998 (KR) .......................... 98-058379
Dec. 24, 1998 (KR) .......................... 98-058380

(51) Int. Cl.[7] ............................................... G01N 3/56
(52) U.S. Cl. .................................................. 73/7
(58) Field of Search ................... 73/7, 865.3, 865.9, 73/117, 117.1

(56) References Cited

U.S. PATENT DOCUMENTS 4,554,824 A * 11/1985 King et al. .................. 73/117
5,282,986 A * 2/1994 Otake et al.
5,394,743 A * 3/1995 Noguchi et al. .............. 73/117
5,465,605 A * 11/1995 Smith et al. ..................... 73/7

* cited by examiner

Primary Examiner—Robert Raevis
(74) Attorney, Agent, or Firm—Christie, Parker & Hale, LLP

(57) ABSTRACT

An apparatus for accurately testing durability of a switch for an automobile in the state that the switch mounted on the instrument panel of the automobile, the apparatus comprises a switch operating means that operates a switch fitted on the instrument panel of an automobile, a jig means for setting the switch operating means to the inside of the automobile, and a control means for controlling operation of the switch operating means.

9 Claims, 6 Drawing Sheets

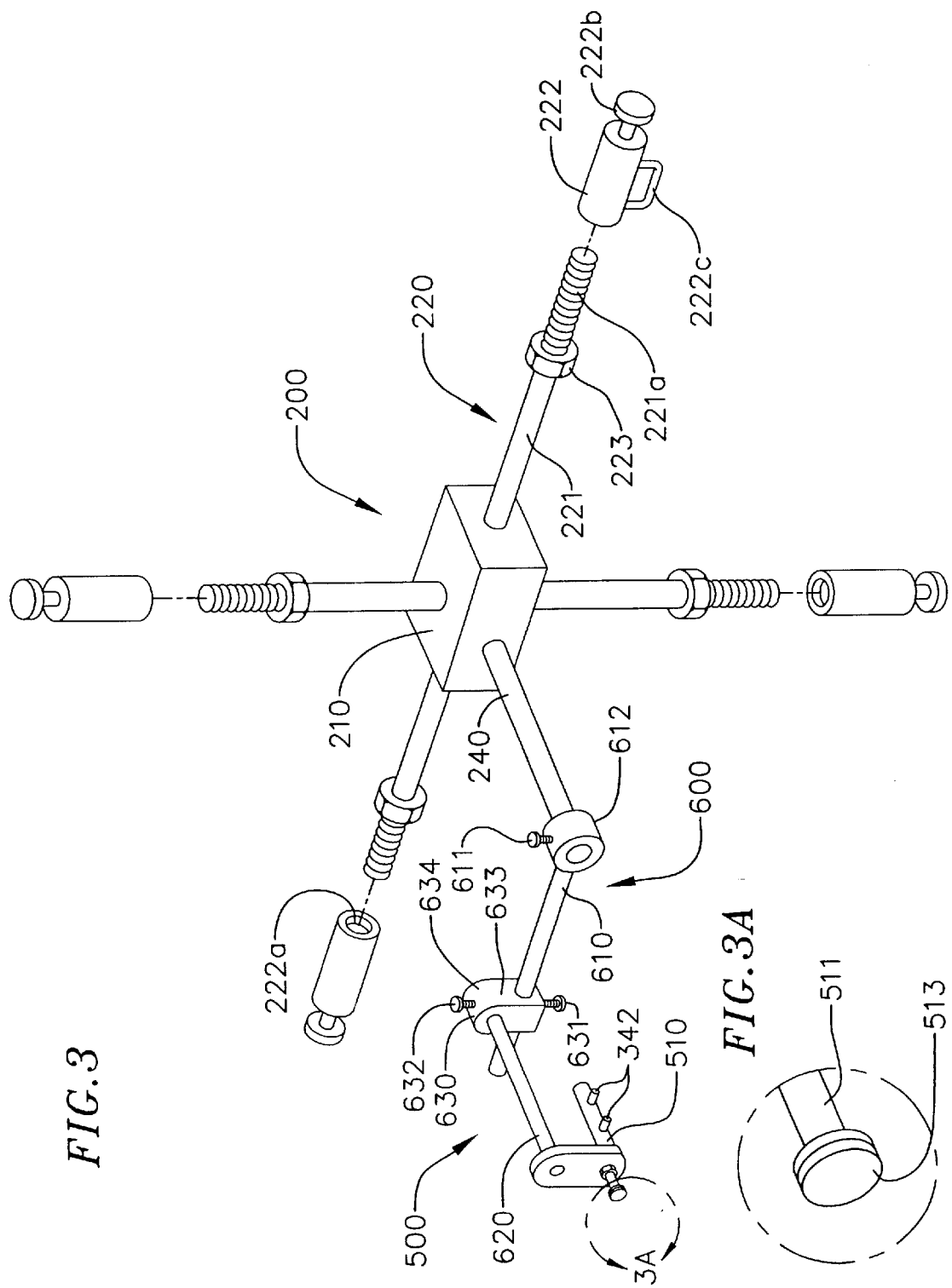

SLIDE-TYPED SWITCH DURABILITY TESTING APPARATUS FOR AUTOMOBILE

FIELD OF THE INVENTION

The present invention relates to an apparatus for testing the durability of the switch of an automobile, more particularly an apparatus for accurately testing the durability of the switch of an automobile in the state that the switch actually mounted on the automobile.

BACKGROUND OF THE INVENTION

Generally on the instrument panel of an automobile are mounted several kind of switches like a select switch for selecting the outside air or the inside air of the automobile, a control switch for controlling the blowing direction of the air, an emergency switch for indicating the emergency state of the automobile, and a switch for operating the thermal heating line of a rear glass.

The switches are typically classified into a sliding type of switch, a push type of switch, and a rotary type of switch according to the operating method.

Then, the switches inevitably become abrasive and finally do not properly operated. Therefore the switches must have enough durability enable to endure the operation work repeated in many times for the life of the automobile.

Until now, the durability of the switches is tested before being fitted to the instrument panel of the automobile.

But the test performed before fitting to the automobile cannot accurately carried out, because the condition of the testing is not matched to the actual condition that the switches are fitted on the instrument panel.

Therefore, a device is required for accurately testing the durability of the switch in condition that the switch is mounted on the instrument panel.

SUMMARY OF THE INVENTION

The object of the present invention is to provide an apparatus for testing the durability of the switches for an automobile in actual state the switches are mounted on the instrument panel.

The present invention to achieve the above object comprises a switch operating means that operates a switch fitted on the instrument panel of an automobile, a jig means for setting the switch operating means to the inside of the automobile, and a control means for controlling operation of the switch operating means.

The switch operating means comprises a holding plate for holding the lever of a sliding type of switch, a cylinder having a piston rod that slides the holding plate, a supporting frame on which the cylinder is mounted, a guide rail for guiding the holding plate on the supporting frame, a stopper for adjusting the working distance of the holding plate, and a supporting bar for engaging the supporting frame with the jig.

The switch operating means comprises a cylinder having a piston pushing the push type of switch repeatedly, a position adjusting mechanism supporting the cylinder to the jig and controlling the position of the cylinder according to the position of the push type of switch, and a supporting bar connecting the position adjusting mechanism to the jig supporting bar connecting the position adjusting mechanism to the jig.

The position adjusting mechanism comprises a rotating rod having a boss connected with the supporting bar, a movable rod fixedly connected with the cylinder; and a position controller having two guide holes through which the rotating rod and the movable rod are inserted.

The switch operating means comprises a rotating holder holding the rotary type of switch, an air motor having a rotating shaft for turning the holder, a supporting plate for mounting the air motor; a stopper for adjusting the rotating angle of the rotating holder; and a supporting bar connecting the supporting plate to the jig.

The rotating plate comprises a housing having a hollow, one end of the housing being connected to the rotating shaft of the air motor and the other of the housing having a guide hole; a transporting rod rotatably jointed with the hollow of the housing and having tooth portions on the both ends thereof respectively; and a holding piece having a boss engaged with the transporting rod through a tooth portion of the boss and a holding pad for holding the rotating type of switch.

The stopper comprises a pivot arm mounted on the rotating shaft of the air motor that is protruded to the opposite side of the supporting plate through a hole pierced in the center thereof; a number of position setting holes arranged around the pierced hole with a regular interval; and a stopper bracket having a hole and connected to the position setting holes of the supporting plate through a bolt.

The jig comprises a mounting body engaged with the supporting bar of the switch operating means; and four setting bars fixed on the four surfaces of the mounting body and being capable of controlling its length.

The setting bar comprises a fixed rod attached on the mounting body with one end thereof and having male tooth portion on the other end thereof; a movable rod having a female tooth portion engaged with the male tooth portion of the fixed rod; a supporting rod elastically supported in the movable rod and a lever used for turning the movable bar; and a locking nut for locking or unlocking the movable rod to the fixed rod.

BRIEF DESCRIPTION OF THE DRAWINGS

The above object and other advantages of the present invention will become more apparent by describing in detail the preferred embodiment of the present invention with reference to the attached drawings in which:

FIG. 3 is a perspective view showing an apparatus for testing a push type of switch for an automobile according the present invention;

FIG. 3A is an enlarged view of the section encircled by arrows 3A in FIG. 3;

DETAILED DESCRIPTION OF THE PRESENT INVENTION

An apparatus in accordance with the present invention comprises a switch operating means 400, 500, 600 that operate a switch 10 fitted on the instrument panel of an automobile, a jig means 200 for setting the switch operating means to the inside of the automobile, and a control means 400 for controlling operation of the switch operating means.

Figure 1:
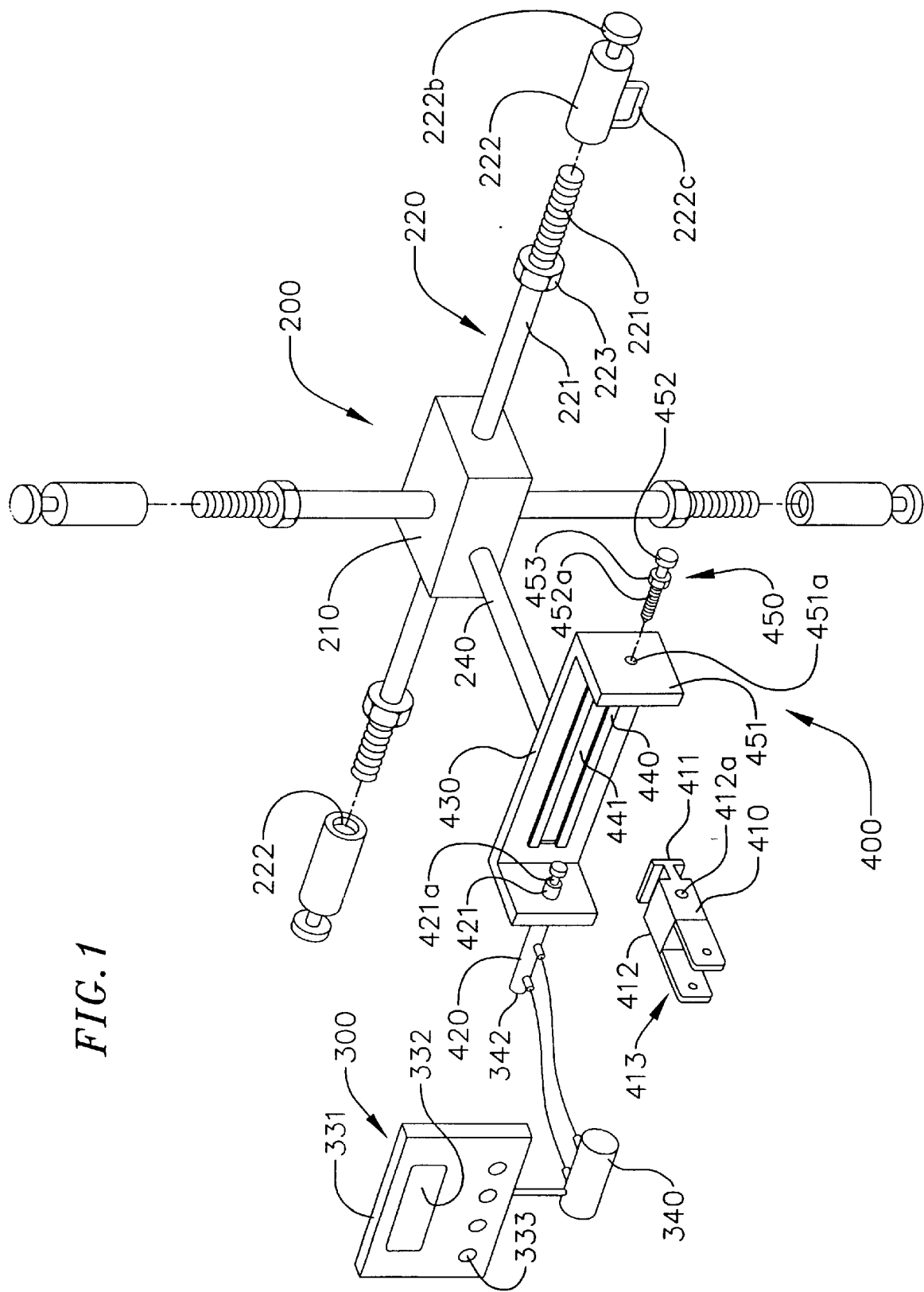
FIG. 1 is a perspective view showing an apparatus for testing a sliding type of switch for an automobile according the present invention.

FIG. 1 shows a sliding type of switch operating means 400 according to the first embodiment of the present invention.

The switch operation means 400 is composed of a holding plate 410 for holding the lever of a sliding type of switch 10, a cylinder 420 having a piston rod 421 that slides the holding plate 410, a supporting frame 430 on which the cylinder 420 is mounted, a guide rail 440 for guiding the holding plate 410 on the supporting frame 430, a stopper 450 for adjusting the working distance of the holding plate 410, and a supporting bar 240 for engaging the supporting frame 430 with the jig 200.

The jig 200 is composed of a mounting body 210 engaged with the supporting bar 240 of the switch operating means 400, and four setting bars 220 fixed on the four surfaces of the mounting body 210 and being capable of controlling its length.

The setting bar 220 is composed of a fixed rod 221 attached on the mounting body 210 with the one end thereof and having a male tooth portion 221a on the other end thereof; a movable rod 222 having a female tooth portion 222a engaged with the male tooth portion 221a of the fixed rod 221, a supporting rod 222b elastically supported in the movable rod 222 and a lever 222c used for turning the movable bar 222; and a locking nut 223 for locking or unlocking the movable rod 222 to the fixed rod 221.

As shown in FIG. 1, the cylinder 420 is mounted on the one end of the supporting frame 430, and the stopper 450 is mounted on the other end of the supporting frame 430. The guide rail 430 is provided on the supporting frame 430.

A guide hole 441 is provided on the guide rail 440 along the longitudinal direction of the guide rail 440, and a slide rib 411 is formed on the end of the holding plate 410 so that the holding plate 410 can slide along the guide rail 440.

A connecting bracket 412 is connected with the piston rod 421 of the cylinder 420, and a holding pad 413 for holding the lever of the slide type of switch 10 is provided on the connecting bracket 412.

The connecting bracket 412 and the piston 421 are engaged with the tooth portions 412a, 421a each other so that the holding plate 410 can be changed, if the size of the switch is changed.

The stopper 450 is comprised of a stopper bracket 451 that is a part of the supporting bracket 430, a stopper shaft 452 having a tooth portion 452a and a locking nut 453 engaged with the tooth portion 452a of the stopper shaft 452. The stopper bracket 451 has a tooth hole 451a, and the stopper shaft 452 is engaged with the tooth hole 451a through the tooth portion 452a.

The sliding distance of the holding plate 410 holding the slide type of switch 10 can be changed by changing the length of the stopper shaft 452 engaged with the stopper bracket 451.

The setting bars 220 are fixed on the right side, the left sides, upside and downside of the mounting body 210 respectively. If necessary the setting bars 220 can be additionally fixed on the front side and the rear side.

The male tooth portion 221a of the fixed rod 221 is engaged with the female tooth portion 222a of the movable rod 222 so that the length of the setting bar 220 can be adjusted by the movement of the male tooth portion 221a and the female portion 222a.

The control means 300 is comprised of a display part 332 and a number of control buttons 333 and controls the direction and amount of the air supplied to the cylinder 420. For example, the air supplied into the cylinder 420 through a port 342 provided on the front end and the rear end of the cylinder 420 is selectively controlled by the air supplying means 340 of the control means 300.

The first embodiment according to the present invention comprised as described above is operated as follow.

First, the seats in the automobile are removed, and then the length of the setting bar 220 in the jig 200 is properly adjusted to the width and the height of the room of the automobile.

Figure 2:
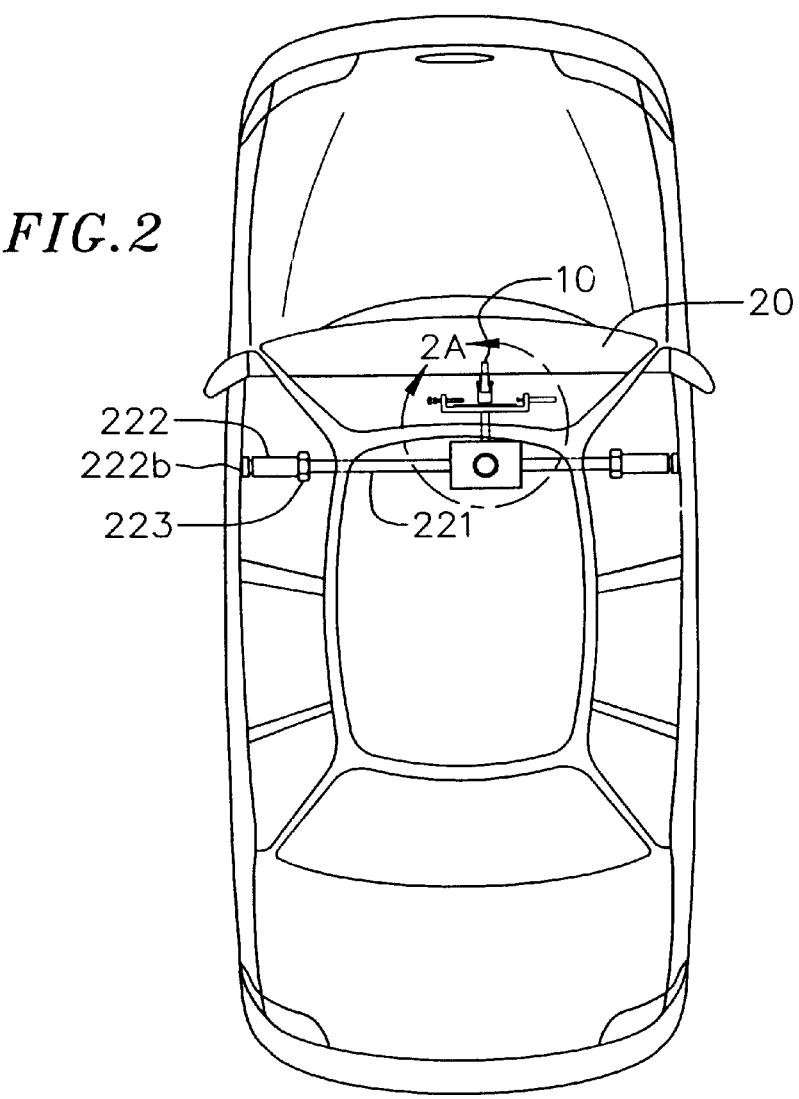
FIG. 2 is a perspective view showing that the apparatus described in FIG. 1 is mounted in the automobile.
Figure 2A:
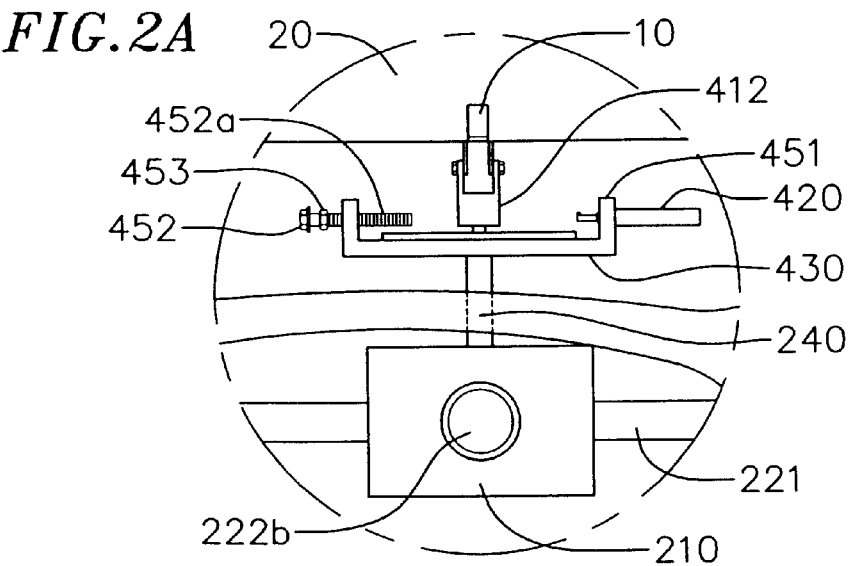
FIG. 2A is an enlarged view of the section encircled by arrows 2A in FIG. 2.
Figure 4:
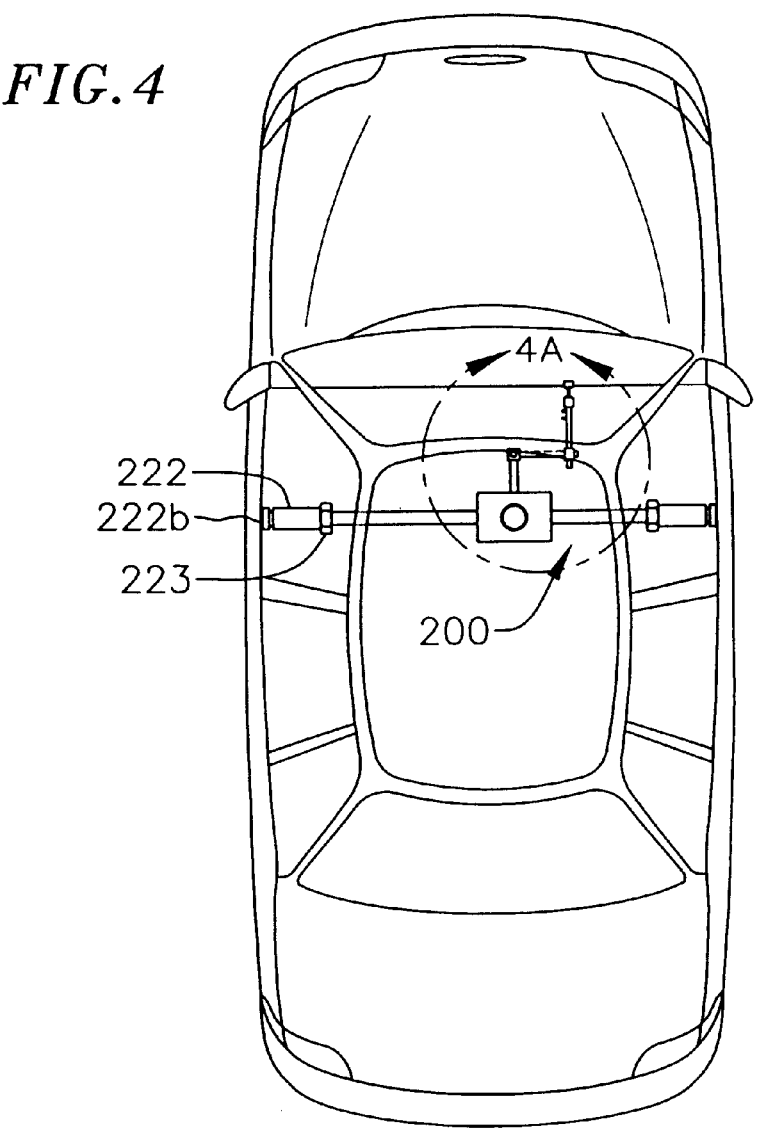
FIG. 4 is a perspective view showing that the apparatus described in FIG. 3 is mounted in the automobile.
Figure 4A:
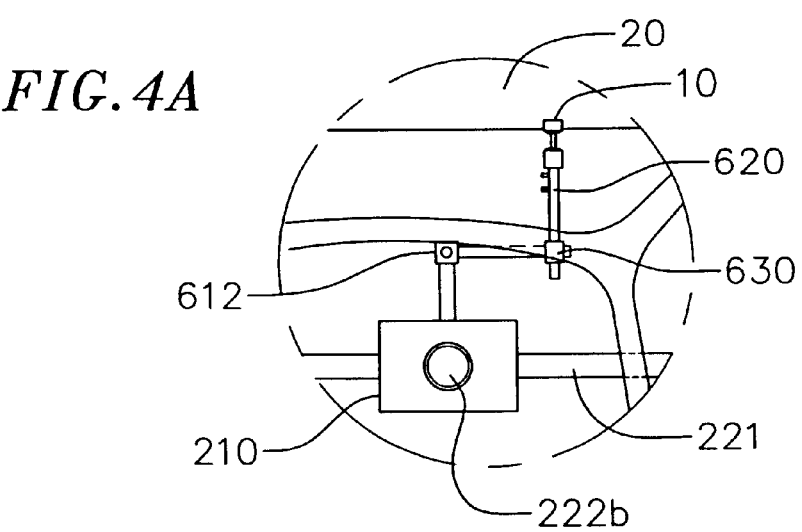
FIG. 4A is an enlarged view of the section encircled by arrows 4A in FIG. 4.

The ends of the setting bars 220 are firmly contacted with the inner wall of the room of the automobile, and the jig 200 is mounted in the room of the automobile as shown in FIG. 2 and FIG. 2A.

Next, the switch operating means 400 is connected to the mounting box 210 of the jig 200 through the supporting bar 240. The slide type of switch 10 mounted on the instrument panel 20 is held by the holding plate 410 of the switching operating means 400.

The air supplying means 340 controlled by the control means 300 adjusts the amount of the air supplied into the cylinder 420 of the switch operating means 400. And then the piston rod 421 of the cylinder 420 works, and the holding plate 410 connected with the end of the piston rod 421 reciprocates.

At this time, the holding pad 413 of the holding plate 410 is elastically bent and softly moves the switch 10 straightly.

The stopper shaft 452 of the stopper 450 adjusts the sliding distance of the holding plate 410 holding the sliding type of switch 10, and the guide rail 440 guides the holding plate 410 to move straightly.

Therefore, the sliding type of switch held on the holding plate 410 also reciprocates toward the left direction and the right direction under the condition that the sliding type of switch 10 is actually mounted on the instrument of the automobile.

As a result of that, the durability of the sliding type of switch can be accurately tested.

FIG. 3, FIG. 3A, FIG. 4 and FIG. 4A, show a push type of switch operating means 500 according to the second embodiment of the present invention.

The push type of switch operating means 500 comprises a cylinder 510 having a piston 511 pushing the push type of switch 10 repeatedly, a position adjusting mechanism 600 supporting the cylinder 510 to the jig 200 and controlling the position of the cylinder 510 according to the position of the push type of switch 10, and a supporting bar 240 connecting the position adjusting mechanism 600 to the jig 200.

The position adjusting mechanism 600 comprises a rotating rod 610 having a boss 612 connected with the supporting bar 240, a movable rod 620 fixedly connected with the cylinder 620, and a position controller 630 having two guide holes 633, 634 through which the rotating rod 610 and the movable rod 260 are inserted.

A locking pin 611 is provided on the boss 612 for locking the rotating rod 610 to the supporting bar 240, and two locking pin 631, 632 are provided on the position controller 360 for locking the movable rod 260 and the rotating rod 610.

Two port 342 for supplying air into the piston 511 are provided on the cylinder 510, and a push damper 513 made of elastic material is provided on the end of the piston 511 for pushing the push type of switch 10.

The cylinder 510 can be moved in front and in rear by moving the movable rod 620 that is guided by the guide hole 634 of the position controller 630, and the cylinder 510 also can be moved in left and in right by changing the position of the position controller 630 that is moved along the rotating rod 610.

Furthermore the cylinder 510 can be moved upward or downward by rotating the rotating rod 610 about the supporting bar 240 through the boss 612.

The locking pin 611 locks or unlocks the rotating rod 610 to the supporting bar 240 after adjusting the height of the cylinder 510 by rotating the rod 610, the locking pin 631 also locks or unlocks the position controller 630 to the rotating rod 610 after adjusting the position of the cylinder 510 by moving the position controller 630 along the rotating rod 610 in right or left, and the locking pin 632 locks or unlocks the movable rod 620 to the position controller 630 after adjusting the position of the cylinder 510 in front and rear.

The jig 220 and the control means (not shown) in the second embodiment according to the present invention are same as the jig 220 and the control means 400 in the first embodiment according to the present invention.

The control means in the second embodiment according to the present invention controls the flow of air supplied into the cylinder 510 and the number of the pushing work of the cylinder 510.

The second embodiment according to the present invention comprised as described above is operated as follow.

As described in the first embodiment of the present invention, the seats in the automobile are removed, and then the length of the setting bar 220 in the jig 200 is properly adjusted to the width and the height of the room of the automobile.

Next, the rotating rod 610 of the switch operating means 500 is joined on the end of the supporting rod 240.

Finally, the position of the cylinder 10 to the push type of switch mounted on the instrument panel of the automobile is properly adjusted, and then the rods 610 and 620 are locked by the locking pins 611, 631, and 632.

After mounting the switch operating means 500 on the jig 200, the control means (not shown) controls the flow of the air supplied into the cylinder 510, and then the piston 511 of the cylinder 510 pushes the push type of switch repeatedly.

Therefore, the push type of switch 10 is tested in the state that the switch 10 is mounted on the instrument of the automobile.

As the result of that, the durability of the push type of switch can be accurately tested.

Figure 5:
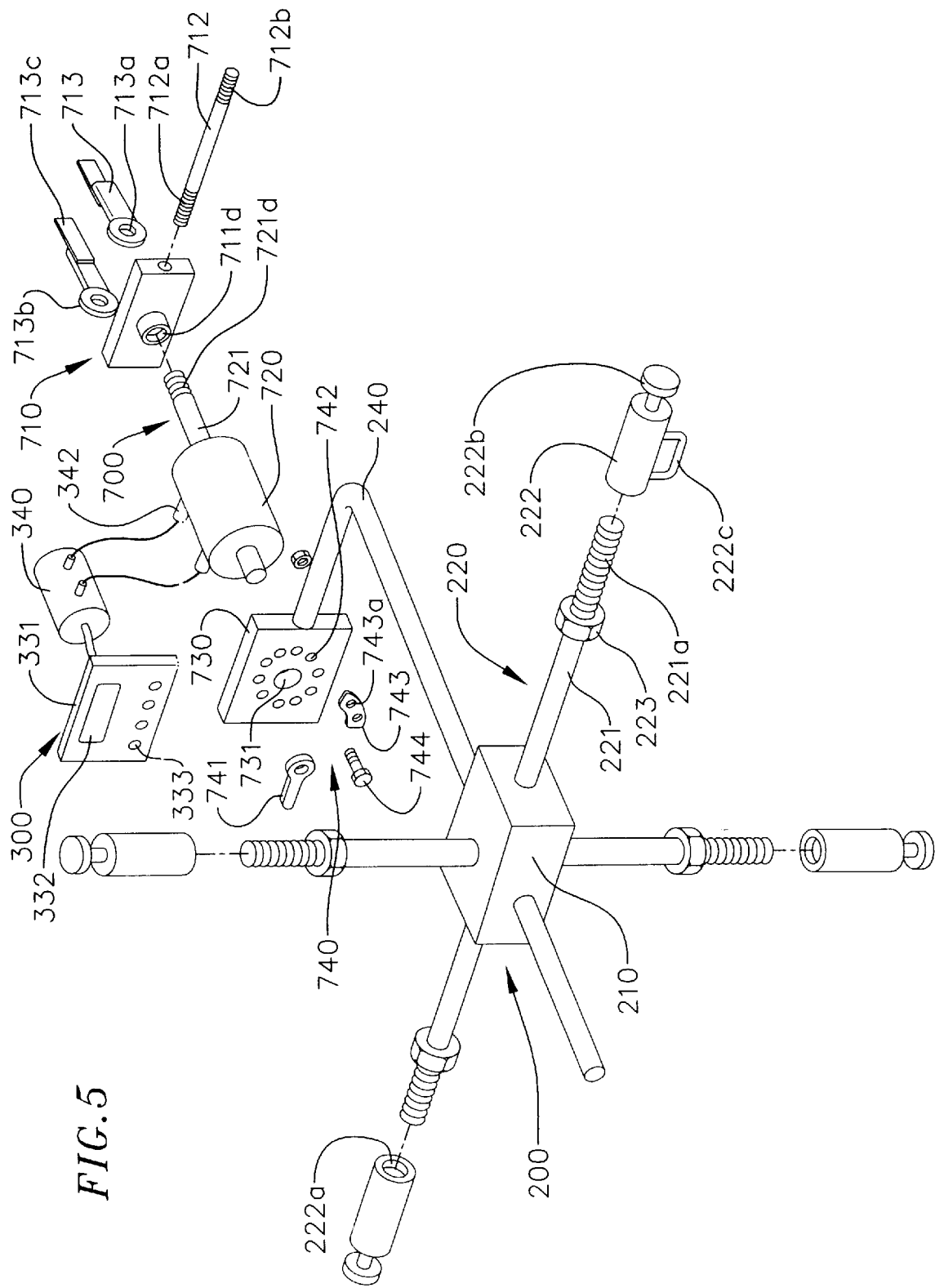
FIG. 5 is a perspective view showing an apparatus for testing a rotary type of switch for an automobile according the present invention.
Figure 6:
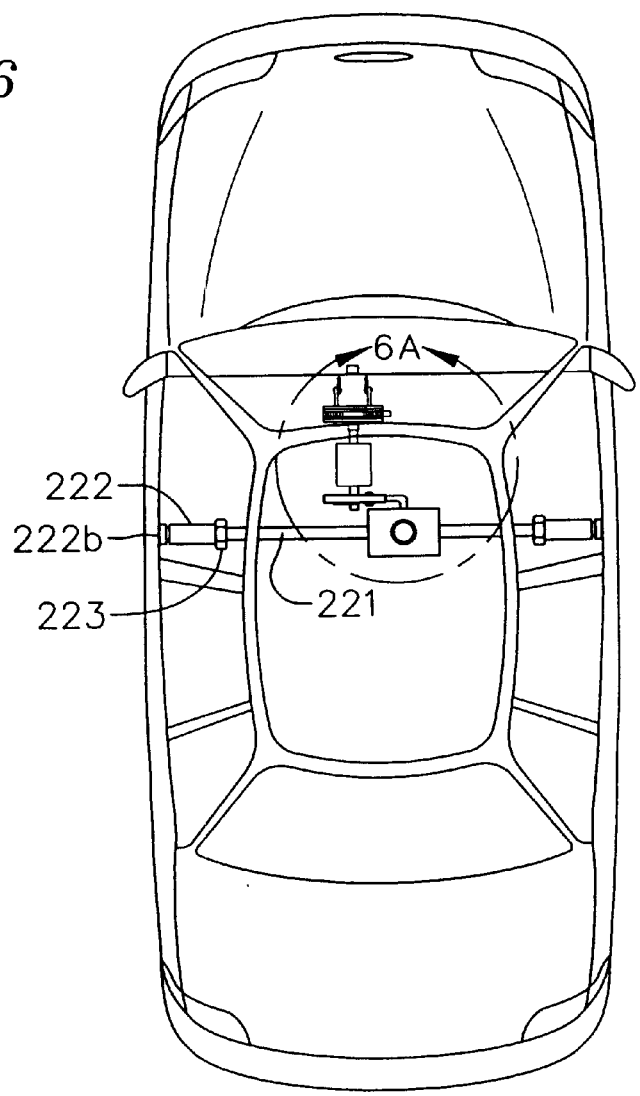
FIG. 6 is a perspective view showing that the apparatus described in FIG. 5 is mounted in the automobile.
Figure 6A:
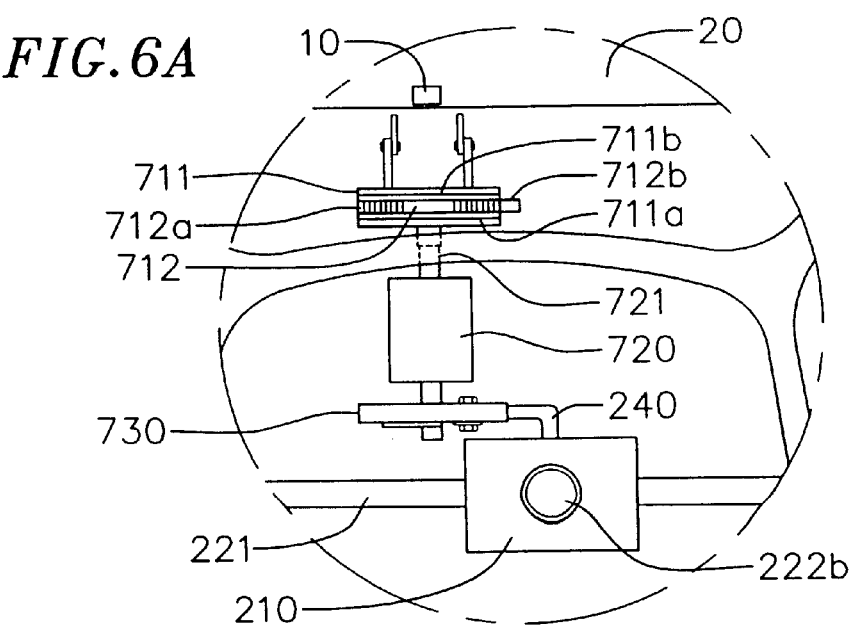
FIG. 6A is an enlarged view of the section encircled by arrows 6A in FIG. 6.

FIG. 5, FIG. 6 and FIG. 6A show a rotary type of switch operating means 700 according to the third embodiment of the present invention.

The rotary type of switch operating means 700 comprises a rotating holder 710 holding the rotary type of switch 10, an air motor 720 having a rotating shaft 721 for turning the holder 710, a supporting plate 730 for mounting the air motor 720, a stopper 740 for adjusting the rotating angle of the rotating holder 710, and a supporting bar 240 connecting the supporting plate 730 to the jig 200.

As shown in FIG. 6, the rotating plate 710 comprises a housing 711 having an opening 711a, one end of the housing 711 being connected to the rotating shaft 721 of the air motor 720 and the other of the housing 711 having a guide hole 711b; a transporting rod 712 rotatably coupled in the opening 711a of the housing 711 and having tooth portions 712a and 712b on the both ends thereof respectively; a holding piece 713 having a boss 713b engaged with the transporting rod 712 through a tooth portion 713a of the boss 713b and a holding pad 713c for holding the rotating type of switch.

The stopper 740 comprises a pivot arm 741 mounted on the rotating shaft 721 of the air motor 720 protruding to the opposite side of the supporting plate 730 through a pierced hole 731 formed on the supporting plate, a number of position setting holes 742 arranged around the pierced hole 731 on the supporting plate with a regular interval, and a stopper bracket 743 having a hole 743a and connected to the position setting hole 742 of the supporting plate 730 by a bolt 744.

On the rear end of the front end of the air motor 720 are provided two ports 342 through which the air for working the air motor is supplied, and the air rotates the rotating shaft 721 of the motor 720. And the air motor 720 is mounted on the supporting plate 731.

The rotating holder 710 moves along the transporting rod 712 and holds the rotary type of switch or releases the switch, when the transporting rod 712 rotates, because the rotating holder 710 is engaged with the tooth portion 712a and 712b of the rotating rod 712.

The rotating shaft 721 of the air motor 720 and the housing 711 are engaged each other with tooth portions 711d and 721d thereof, and the rotating holder 710 can be changed if necessary. For example, when the size of the switch to be test is changed, the rotating holder 710 can be changed to the other rotating holder.

The rotating angle of the plate 710 engaged with the rotating shaft 721 is determined by the rotating angle of the pivot arm 741, and the rotating angle of the pivot arm 741 is determined by the position of the stopper bracket 743 selectively connected to one of the position setting holes 742 of the supporting plate 730.

The jig 200 and the control means (not shown) adopted in this third embodiment of the present invention are same as those of the first embodiment of the present invention.

The switch operating means 700 controls the flow of the air supplied into the air motor 720, the number of the rotating operation of the shaft 721 and the working time etc.

The third embodiment according to the present invention comprised as described above is operated as follow.

As described in the first embodiment of the present invention, firstly the seats in the automobile are removed, and then the length of the setting bar 220 in the jig 200 is properly adjusted to the width and the height of the room of the automobile.

Next, the supporting 240 jointed with the supporting plate 730 of the switch operating means 700 is connected to the mounting body 210 of the jig 200.

Finally, the position of the cylinder 10 to the rotary type of switch mounted on the instrument panel of the automobile is properly adjusted and the holding piece 713 of the rotating holder 710 holds the rotary type of switch 10 mounted on the instrument panel 20.

After arranging the switch operating means 700 on the jig 200, the air supplying means 340 of the control means 300 controls the flow of the air supplied into the air motor 720 of the switch operating means 700.

Then the air motor 720 rotates the rotating plate 710 to certain degree, and then the holding pad 713c of the rotating plate 710 rotates the rotary type of switch 10 mounted on the instrument panel of the automobile.

At this time, the holding piece 713 of the rotating holder 710 is elastically bent and softly rotates the rotary type of switch 10.

Both the rotating arm 741 of the stopper 740 and the stopper bracket 743 control the degree of an angle of the rotating holder 710 that rotates the rotary type of switch 10.

Therefore, the rotary type of switch 10 is tested in the state that the switch 10 is mounted on the instrument panel of the automobile.

As the result of that, the durability of the rotary type of switch can be accurately tested.

What is claimed is:

1. An apparatus for testing durability of a switch for an automobile, the apparatus comprising:
    a switch operating means that operates a switch fitted on an instrument panel of an automobile;
    a jig for setting the switch operating means to the inside of the automobile; and
    a control means for controlling operation of the switch operating means.

2. An apparatus for testing durability of a switch for an automobile according to claim 1, wherein the switch operating means comprises:
    a holding plate for holding the lever of a sliding type of switch;
    a cylinder having a piston rod coupled to the the holding plate;
    a supporting frame on which the cylinder is mounted;
    a guide rail for guiding the holding plate on the supporting frame;
    a stopper for adjusting the working distance of the holding plate; and
    a supporting bar for engaging the supporting frame with the jig.

3. An apparatus for testing durability of a switch for an automobile according to claim 1, wherein the switch operating means comprises:
    a cylinder having a piston pushing a push type of switch repeatedly;
    a position adjusting mechanism supporting the cylinder to the jig and controlling the position of the cylinder according to the position of the push type of switch; and
    a supporting bar connecting the position adjusting mechanism to the supporting bar connecting the position adjusting mechanism to the jig.

4. An apparatus for testing durability of a switch for an automobile according to claim 3, wherein the jig comprises:
    a mounting body engaged with the supporting bar of the switch operating means; and
    four setting bars fixed on four surfaces of the mounting body.

5. An apparatus for testing durability of a switch for an automobile according to claim 4, wherein each setting bar comprises:
    a fixed rod attached on the mounting body with one end thereof and having male tooth portion on the other end thereof;
    a movable rod having a female tooth portion engaged with the male tooth portion of the fixed rod;
    a supporting rod elastically supported in the movable rod and a lever used for turning the movable rod; and
    a locking nut for locking or unlocking the movable rod to the fixed rod.

6. An apparatus for testing durability of a switch for an automobile according to claim 3, wherein the position adjusting mechanism comprises:
    a rotating rod having a boss connected with the supporting bar;
    a movable rod fixedly connected with the cylinder; and
    a position controller having two guide holes through which the rotating rod and the movable rod are inserted.

7. An apparatus for testing the durability of a switch for an automobile according to claim 1, wherein the switch operating means comprises:
    a rotating holder holding a rotating type of switch,
    an air motor having a rotating shaft for turning the holder;
    a supporting plate for mounting the air motor;
    a stopper for adjusting the rotating angle of the rotating holder; and
    a supporting bar connecting the supporting plate to the jig.

8. An apparatus for testing durability of a switch for an automobile according to claim 7, wherein the rotating plate comprises:
    a housing having an opening and two ends, one end of the housing being connected to the rotating shaft of the air motor and the other end of the housing having a guide hole;
    a transporting rod rotatably coupled with the opening of the housing and having tooth portions on the both ends thereof respectively; and
    a holding piece having a boss engaged with the transporting rod through a tooth portion of the boss and a holding pad for holding the rotating type of switch.

9. An apparatus for testing durability of a switch for an automobile according to claim 7, wherein the stopper comprises:
    a pivot arm mounted on a portion of the rotating shaft of the air motor that protrudes through a hole formed in the supporting plate;
    a number of position setting holes formed on the supporting plate and arranged around the pierced hole with a regular interval; and
    a stopper bracket having a hole and connected to a position setting hole of the supporting plate through a bolt.

* * * * *